United States Patent [19]

Thornton et al.

[11] Patent Number: 5,014,287
[45] Date of Patent: May 7, 1991

[54] PORTABLE X-RAY FLUORESCENCE SPECTROMETER FOR ENVIRONMENTAL MONITORING OF INORGANIC POLLUTANTS

[76] Inventors: Michael G. Thornton, 10073 Jasmine Ct., Littleton, Colo. 80125; Benton C. Clark, III, 10890 Park Range Rd., Littleton, Colo. 80127

[21] Appl. No.: 510,572

[22] Filed: Apr. 18, 1990

[51] Int. Cl.$^5$ .......................................... G01N 23/223
[52] U.S. Cl. .......................................... 378/45; 378/49; 378/83; 250/369
[58] Field of Search ...................... 250/310, 369, 366; 378/45, 49, 83, 93

[56] References Cited

U.S. PATENT DOCUMENTS

| | | | |
|---|---|---|---|
| 3,806,726 | 4/1974 | Ishijima | 378/83 |
| 3,878,392 | 4/1975 | Yew et al. | 250/306 |
| 3,919,549 | 11/1975 | Sahores et al. | 250/310 |
| 4,063,089 | 12/1977 | Gamba | 250/272 |
| 4,200,796 | 4/1980 | Murakami et al. | 378/93 |
| 4,358,854 | 11/1982 | Marten et al. | 378/45 |
| 4,362,935 | 12/1982 | Clark, III | 378/48 |
| 4,388,530 | 6/1983 | Lubecki et al. | 378/45 |
| 4,417,355 | 11/1983 | Anisovich et al. | 378/83 |
| 4,426,717 | 1/1984 | Schwenke et al. | 378/45 |
| 4,429,409 | 1/1984 | Berry et al. | 378/45 |
| 4,510,573 | 4/1985 | Boyce et al. | 364/498 |
| 4,519,092 | 5/1985 | Albert | 378/45 |
| 4,686,694 | 8/1987 | Berry et al. | 378/120 |
| 4,796,284 | 1/1989 | Jenkins | 378/49 |

OTHER PUBLICATIONS

*Kevex Analyst* 6700, Kevex Corporation, 1101 Chess Dr., Foster City, Calif. 94404 (1982).

Primary Examiner—Edward P. Westin
Assistant Examiner—Kim-Kwok Chu
Attorney, Agent, or Firm—Dorr, Carson, Sloan & Peterson

[57] ABSTRACT

A portable x-ray fluorescence spectrometer has a portable sensor unit containing a battery, a high voltage power supply, an x-ray tube which produces a beam x-ray radiation directed toward a target sample, and a detector for fluorescent x-rays produced by the sample. If a silicon-lithium detector is used, the sensor unit also contains either a thermoelectric or thermochemical cooler, or a small dewar flask containing liquid nitrogen to cool the detector. A pulse height analyzer ("PHA") generates a spectrum of data for each sample consisting of the number of fluorescent x-rays detected as a function of their energy level. The PHA can also store spectrum data for a number of samples in the field. A processing unit can be attached to the pulse height analyzer to upload and analyze the stored spectrum data for each sample. The processing unit provides a graphic display of the spectrum data for each sample, and provides qualitative and/or quantitative analysis of the elemental composition of the sample by comparing the peaks in the sample spectrum against known x-ray energies for various chemical elements. An optional filtration enclosure can be used to filter particles from a sample suspension, either in the form of a natural suspension or a chemically created precipitate. The sensor unit is then temporarily attached to the filtration unit to analyze the particles collected by the filter medium.

22 Claims, 6 Drawing Sheets

PORTABLE X-RAY FLUORESCENCE SPECTROMETER FOR ENVIRONMENTAL MONITORING OF INORGANIC POLLUTANTS

BACKGROUND OF THE INVENTION

The invention described herein was made in the performance of work under NASA Contract No. NAS 1-15942, and is subject to the provisions of Section 305 of the National Aeronautics and Space Act of 1958 as amended (42 U.S.C. 2457)

1. FIELD OF THE INVENTION

The present invention relates generally to the field of element analysis systems, and specifically to the field of portable x-ray fluorescence spectrometers.

2. STATEMENT OF THE PROBLEM

Environmental monitoring to determine the presence of hazardous inorganic pollutants is a difficult, time consuming, and expensive task. Currently, samples must be collected from the contaminated site and sent to a laboratory for analysis. Results of such analyses are typically returned in about 3 weeks. The present invention allows many types of samples to be analyzed on site, with analysis results within minutes. Sample preparation is minimal or unnecessary. On site analysis largely eliminates potential disputes concerning sample identification or its chain of custody. Overall site cleanup costs can be reduced by eliminating the need for repeat trips to the same site to clean up hot spots of contamination. The present invention would allow cleanup crews to determine in a few minutes exactly where additional effort is required, instead of waiting several weeks for the results of laboratory tests to confirm the effectiveness of the cleanup operation.

A number of devices and processes have been invented in the past relating to x-ray fluorescence systems used for element identification and analysis, including the following:

| Inventor | Patent No. | Issue Date |
| --- | --- | --- |
| Clark | 4,362,935 | Dec. 7, 1982 |
| Gamba | 4,063,089 | Dec. 13, 1977 |
| Lubecki, et al. | 4,388,530 | June 14, 1983 |
| Berry, et al. | 4,429,409 | Jan. 31, 1984 |
| Berry, et al. | 4,686,694 | Aug. 11, 1987 |
| Boyce, et al. | 4,510,573 | Apr. 9, 1985 |
| Jenkins | 4,796,284 | Jan. 3, 1989 |

Literature describing the "Kevex Analyst 6700" sold by Kevex Corporation of Foster City, Calif.

Clark discloses a field portable x-ray fluorescent spectrometer having a plurality of interchangeable sensor heads. Each sensor head has a shutter which, when open, permits one of several radiation sources (i.e. radioisotopes) to irradiate a material to be analyzed. The fluorescent x-ray radiation is detected by corresponding detectors and analyzed by a multichannel analyzer.

Gamba discloses a portable field x-ray chemical analyzer in which a radioisotope source and an x-ray detector are housed within a probe housing that is attached by flexible connectors to a remote multichannel analyzer, power supply and cryogenic station.

Lubecki, et al., disclose an x-ray fluorescence apparatus in which a radiation source 2 excites a target 4 to produce x-rays which pass through a slurry. A detector located on the other side of the slurry absorbs the radiations emerging from the slurry to determine its elemental content.

The Berry, et al., patents disclose a portable x-ray fluorescence device which includes a hand-held probe unit containing a radiation source for irradiating the sample, and a radiation detector to sensing the fluorescent x-rays emitted by the sample. The probe communicates through a universal asynchronous receiver transmitter with a remote electronic unit which processes and analyses the data from the radiation detector.

Boyce, et al. disclose an algorithm for performing x-ray fluorescence analysis where the physical relationship between the source/detector and the object being examined is not controlled.

Jenkins discloses an x-ray spectrometer in which x-rays are dispersed by a polycrystalline analyzer as a function of the x-ray's wavelength.

In addition to these references, an x-ray analyzer known as the "Kevex Analyst 6700" is sold by Kevex Corporation, 1101 Chess Drive, Foster City, Calif. 94404. It is believed that this device has an x-ray tube and detector housed within a hand-held probe unit. This probe unit is tethered by a long cable to its power supply and to a processing unit for analysis of the data.

3. SOLUTION TO THE PROBLEM

Traditionally, x-ray fluorescence spectrometers have been large, bulky devices intended for use in the laboratory. Smaller x-ray fluorescence spectrometers have been used in interplanetary exploration, such as Viking probe sent to Mars. With the exception of the Kevex device, all of the prior art devices discussed above, that are portable, rely on radioisotopes as radiation sources to excite the sample to produce fluorescent x-rays. However, radioisotopes present major problems in complying with governmental regulations restricting transportation and ultimate disposal of the unit. Furthermore, several different radioisotopes are typically needed to produce a full spectrum of fluorescent x-rays from a sample. This adds substantial complexity to such devices by requiring multiple radioisotopes with separate shutters and detectors, as shown in the Clark patent. The Kevex device uses an x-ray tube as a radiation source in a hand-held probe, but the probe is tethered by a cable to its power source and the processing unit. This substantially limits the use of this device in the environmental monitoring where a truly portable system is necessary. In summary, none of these prior art references show a field-portable x-ray fluorescence spectrometer in which an x-ray tube is used as the radiation source.

SUMMARY OF THE INVENTION

This invention provides a portable x-ray fluorescence spectrometer having a portable sensor unit containing a battery, a high voltage power supply, an x-ray tube which produces a beam x-ray radiation directed toward a target sample, and a detector for fluorescent x-rays produced by the sample. If a silicon-lithium detector is used, the sensor unit also contains a thermoelectric or thermochemical cooler, or a small dewar flask containing liquid nitrogen to cool the detector. A pulse height analyzer ("PHA") generates a spectrum of data for each sample consisting of the number of fluorescent x-rays detected as a function of their energy level. The PHA can also store spectrum data for a number of samples in the field. A processing unit can be attached to the pulse height analyzer to upload and analyze the stored spectrum data for each sample. The processing unit provides a graphic display of the spectrum data for each sample, and provides qualitative and/or quantitative analysis of the elemental composition of the sample by comparing the peaks in the sample spectrum against known peaks for various chemical elements. An optional filtration enclosure can be used to filter particles from a sample suspension. The filtration enclosure is used to filter particles not only from a naturally occurring suspension, but also to filter particles from a chemically created precipitate. This achieves much higher elemental sensitivities by extracting the metal ions in solution into a filterable solid phase collected on the filter medium. The sensor unit is then temporarily attached to the filtration unit to analyze the particles collected by the filter medium.

A primary object of the present invention is to provide an x-ray fluorescence spectrometer that can be readily transported by one person to remote locations to provide on-site analysis of inorganic pollutants.

Another object of the present invention is to provide an x-ray fluorescence spectrometer that can quickly provide or site quantitative or qualitative elemental analysis of a sample, without removal or disturbance of the sample, and without the need to wait for results from a distant laboratory. This permits rapid and efficient mapping of an investigation site to provide a preliminary assessment of the boundaries and severity of contamination.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, wherein.

DETAILED DESCRIPTION OF THE INVENTION

Whenever x-rays strike an object, they stimulate atoms in the object to emit other, lower energy "fluorescent" x-rays. A similar phenomenon can be observed when ultraviolet light stimulates glowing colors, or fluorescences, in certain minerals. This ultraviolet fluorescence exists only in a limited number of specific minerals, whereas x-ray fluorescence occurs in all atoms, and causes the individual elements in a sample to emit regardless of the mineralogical form in which they are combined.

Every element emits fluorescent x-rays at distinctive energies different from those of every other element. The counting rate, or emission intensity, of these distinctive energy levels is proportional to the amount of the element present in the sample. Thus, trace contaminants produce very low levels of emissions compared to major elements in the sample, but the energies of the characteristic x-rays are totally independent of the concentration level. With proper calibration curves, the elemental composition of a sample can be determined from a knowledge of the energies and relative intensities of the fluorescent x-rays. To allow for those factors which affect the intensities of all peaks equally (such as the strength of the excitation source, sample density, and the distance to the sample) it is possible to standardize all measurements relative to the strength of the "backscatter peak." This peak is the one at the highest energy in the spectrum, and is produced as a result of those x-rays that scatter back out of the sample before undergoing a fluorescence-producing interaction with the sample.

Each element produces several distinctive fluorescent x-rays. K lines are the highest x-ray energy an atom can emit. L lines are emitted as x-rays of nearly equal intensity (and some minor lines as well), but of considerably lower energy than the K lines. The following is a table of emissions for a number of toxic elements for the energy range of 3 to 20 keV, the nominal operating range of the preferred embodiment of the present invention:

| Element | Principal Lines* | Energy (keV) |
| --- | --- | --- |
| Cr | K | 5.41 |
| Ni | K | 7.48 |
| Cu | K | 8.05 |
| Zn | K | 8.64 |
| As | K | 10.54 |
| Sc | K | 11.22 |
| Ag | L | 2.98, 3.15 |
| Cd | L | 3.13, 3.32 |
| Sb | L | 3.60, 3.84 |
| Ba | L | 4.47, 4.83 |
| Hg | L | 9.99, 11.82 |
| Tl | L | 10.27, 12.21 |
| Pb | L | 10.55, 12.61 |

*K-alpha-1 line emissions, L-alpha and L-beta line emissions.

Figure 4:
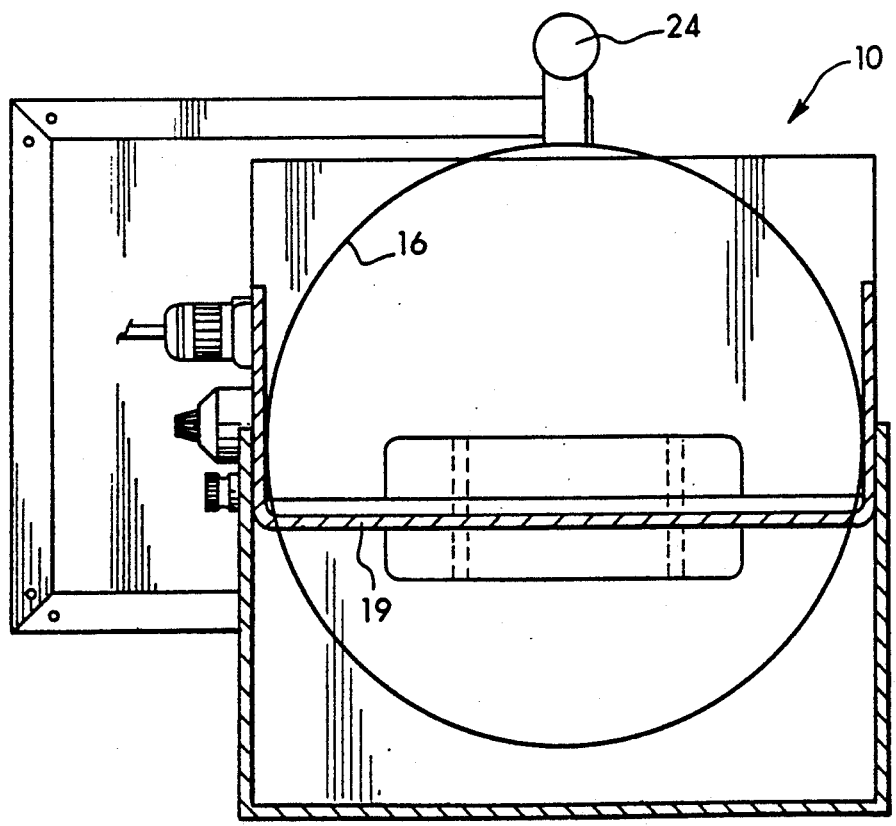
FIG. 4 is a rear view corresponding to FIG. 1.
Figure 5:
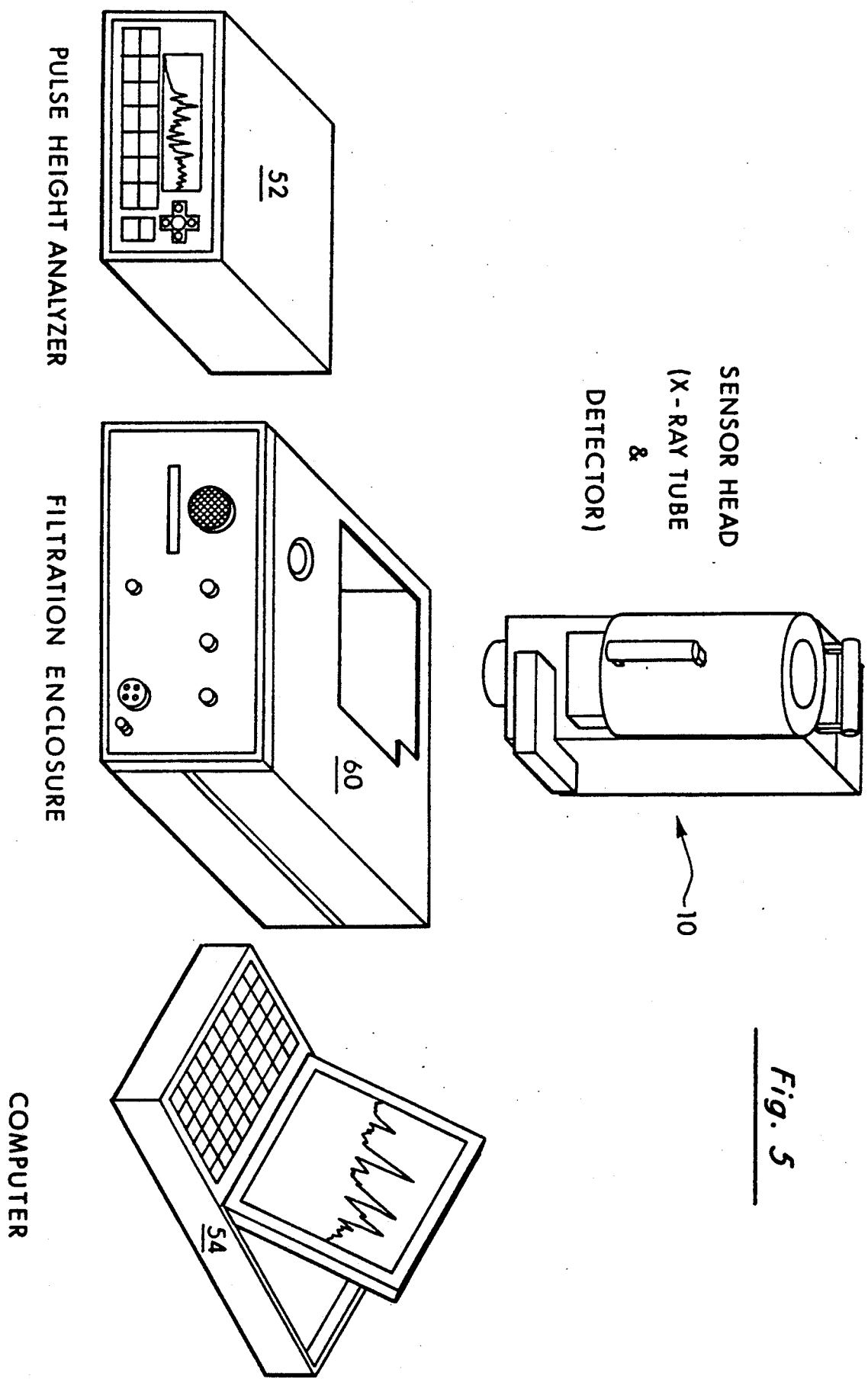
FIG. 5 is a simplified diagram showing all of the components of the present system.

The present invention is composed of several discrete subsystems that provide for sample excitation, fluorescent x-ray detection, data acquisition and storage, filtration of water samples, and computer data processing, as shown in FIG. 5. The first subsystem is the sensor unit 10 containing an x-ray tube 11, battery 18, high voltage power supply 17, x-ray detector 15, and cryogenic storage tank 16, as shown in FIGS. 1-4. In the preferred embodiment of the present invention, the method of exciting x-ray fluorescence in the sample is the x-ray tube 11 which is powered by the high voltage power supply 17, which in turn is powered by rechargeable lead-zinc "Gel-cell" batteries 18. The x-ray tube 11 employed here is a molybdenum targeted tube operated at −30,000 volts. The principal emissions are the Mo K-alpha line at 17.5 keV and the K-beta-1 line at 19.6 keV. A molybdenum foil filter reduces low energy bremsstrahlung x-rays, but these wide spectrum x-rays do persist in the 15-20 keV and 25-30 keV regions. The window 12 of the x-ray tube 11 is positioned to direct a beam of x-rays outward through an aperture 13 in the housing of the sensor unit 10 in a predetermined geometry toward a sample.

Figure 1:
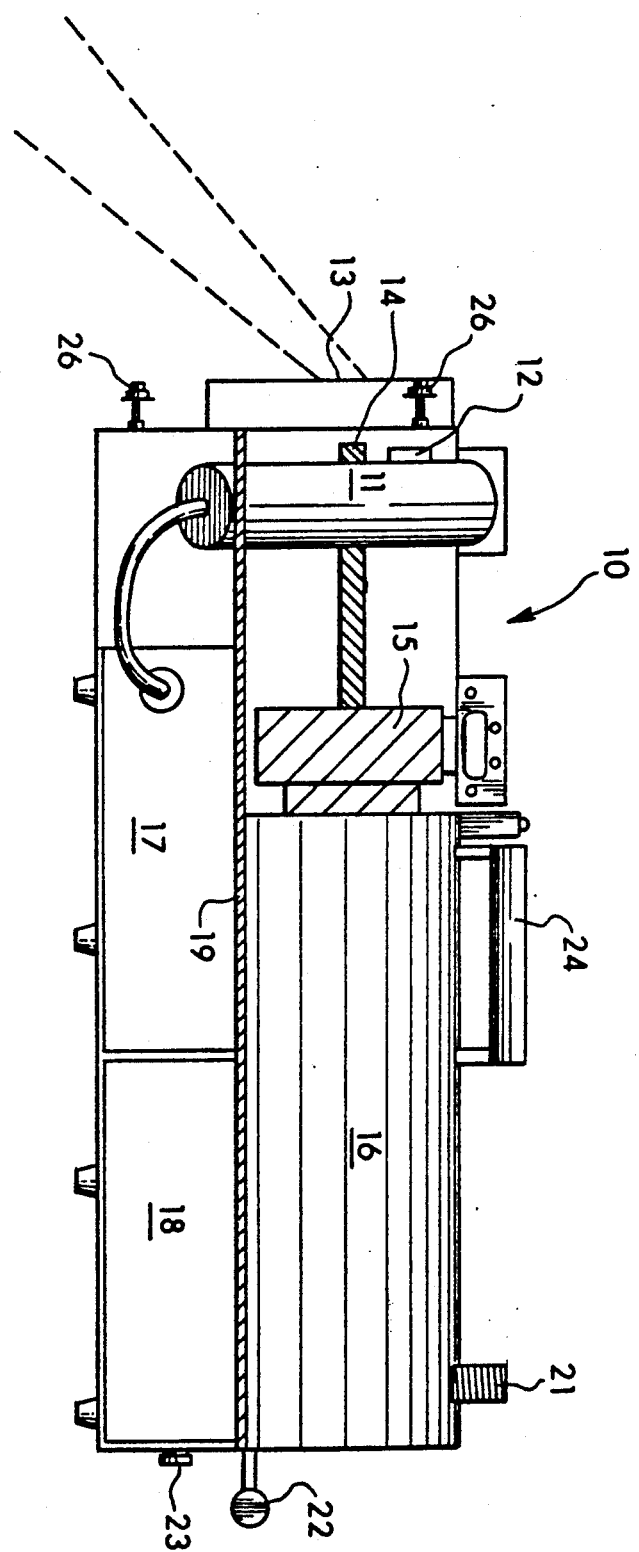
FIG. 1 is a side cross-sectional view of the sensor portion of the system.
Figure 2:
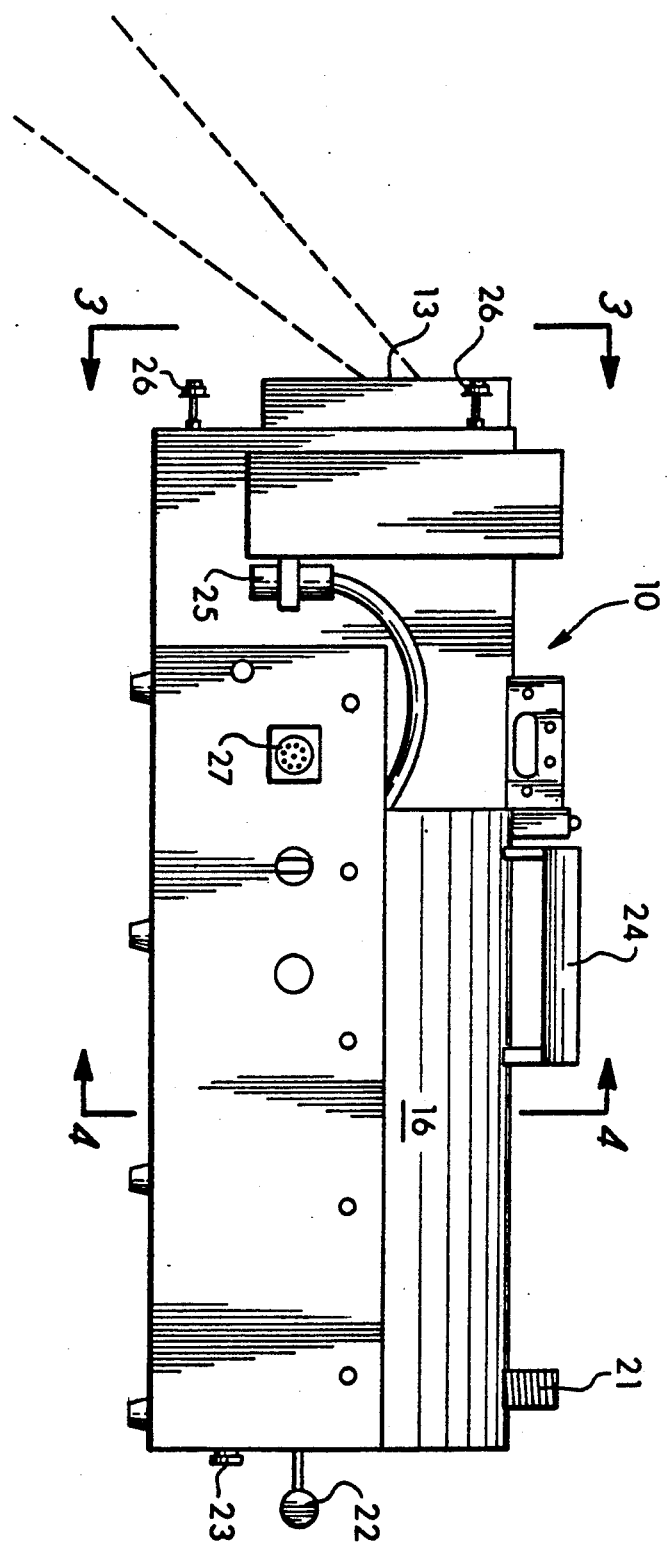
FIG. 2 is a side view corresponding to FIG. 1.
Figure 3:
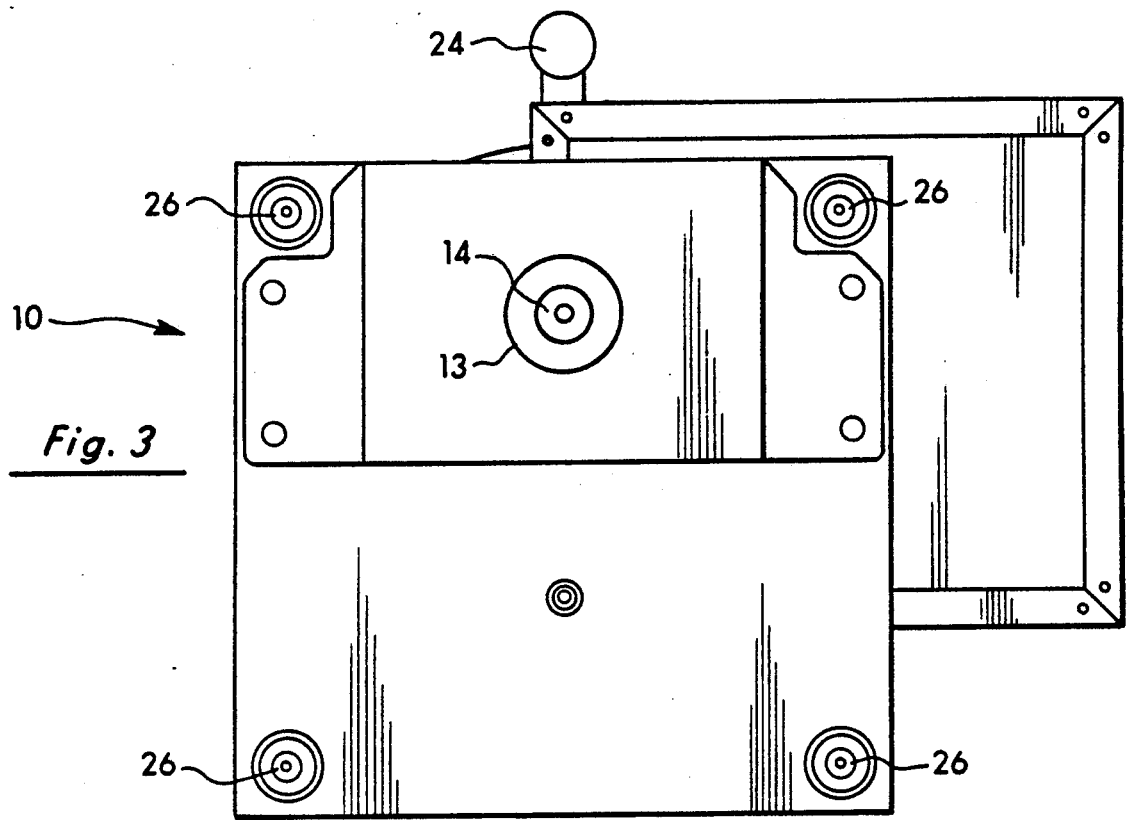
FIG. 3 is a front view corresponding to FIG. 1.

The sensor unit 10 also contains an x-ray detector 15 to detect fluorescent x-rays returned from the sample. The port 14 of the x-ray detector 15 can be aligned, as shown in FIG. 1, to use the same aperture 14 as the x-ray tube 11. In the preferred embodiment, the x-ray detector 15 is a lithium-drifted silicon semiconductor device. An electrical pulse is produced by the detector 15 for each x-ray photon detected. The magnitude of each pulse is a function of the energy level of the x-ray photon. This data is then analyzed by a pulse height analyzer ("PHA") to produce a spectrum of the emitted and scatter x-rays from the sample. The silicon lithium detector has the advantage of producing sharp peaks with a spectral separation superior to proportional counters or scintillation counter spectrometers. However, it has the disadvantage that the Si(Li) chip must be cooled to temperatures in the neighborhood of liquid nitrogen in order to produce this resolution. To provide this cooling, the sensor unit contains either a thermoelectric cooler, a thermochemical cooler, or a small cryogenic storage tank 16, such as a dewar flask, to hold liquid nitrogen to cool the x-ray detector. This storage tank holds sufficient liquid nitrogen to last about 16 hours in the field.

The housing of the sensor unit 10 is typically made of sheet metal to maximize durability in the field, and to minimize electrical interference with the internal components. In particular, the x-ray detector 15 is highly sensitive to electromagnetic interference. The interior of the sensor unit housing is divided into at least two separate chambers by a metal panel 19 to provide electrical shielding between the high voltage power supply 17 and the x-ray detector 15, as shown in FIGS. 1 and 4.

A number of other components of the sensor unit 10 are also shown in FIGS. 1–4. An inlet 21 is provided to permit the storage tank 16 to be vented and refilled. A number of handles 22 and 24 facilitate carrying of the sensor unit by one person. The battery 18 can be recharged by means of an external connector 23. A connector 25 is the output from the batteries 18. In normal operation in the field, this connector 25 is plugged into a mating connector 27 to power the high voltage power supply 17 of the sensor unit 10. A number of feet 26 are attached to the end of the sensor unit 10 to permit the aperture 13 to be placed adjacent to ground samples.

Figure 7:
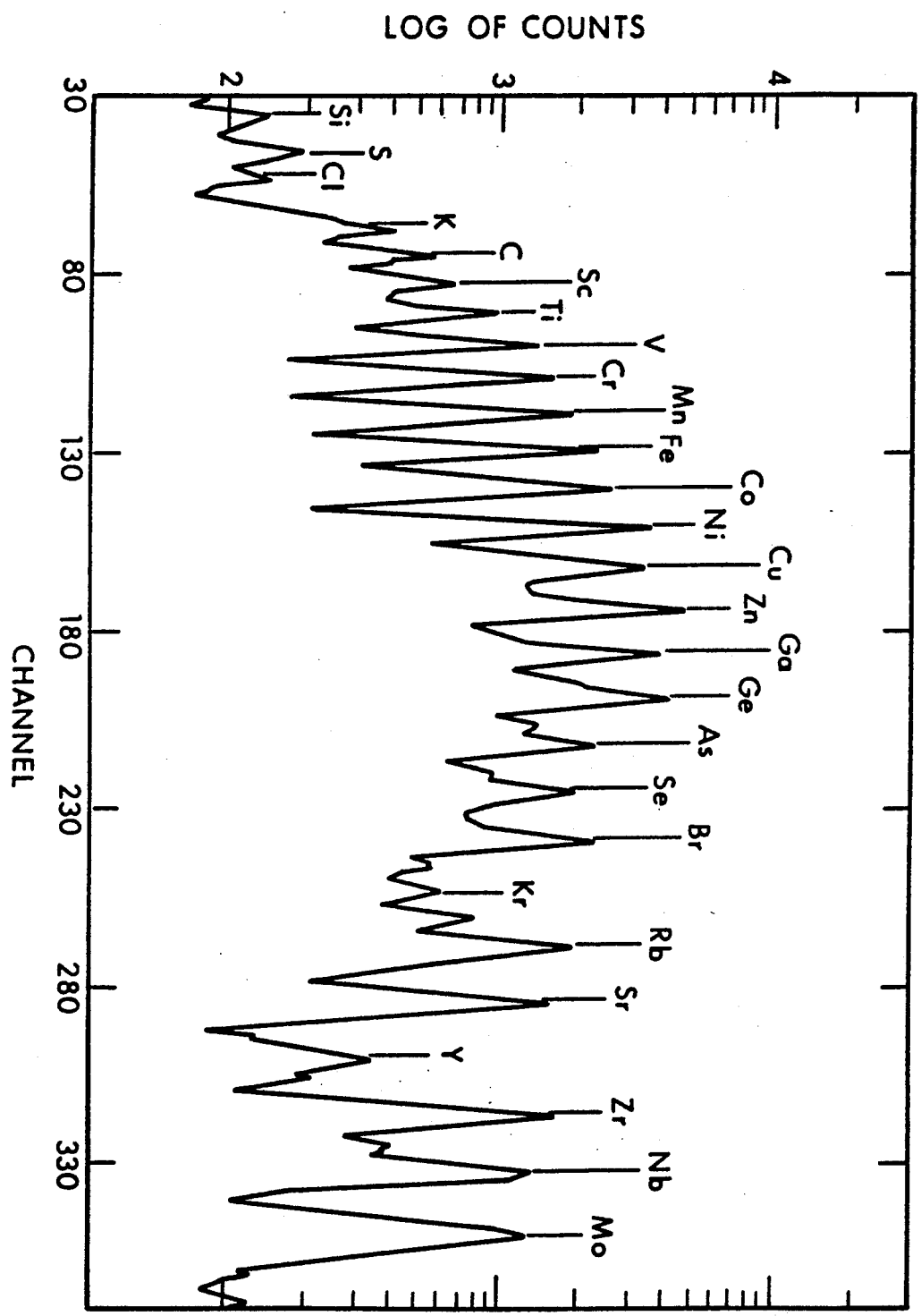
FIG. 7 is an example of an x-ray fluorescence spectrum generated by the present system.

The second subsystem shown in FIG. 5 is the pulse height analyzer 52 ("PHA"). The PHA is connected by a cable to the output terminal of the x-ray detector 15 in the sensor unit 10. Each pulse produced by the x-ray detector 15 is analyzed by the PHA to produce a spectrum of data in which the number of x-ray photons detected are counted for each energy level. A graphical representation of a sample spectrum of such data is shown in FIG. 7. The Canberra Series 10 pulse height analyzer has been found to be suitable for this purpose. This unit is battery powered and is sufficiently portable that it can be carried with the sensor unit in the field. The PHA can also provide temporary storage of spectrum data for a number of samples. For example, the Canberra Series 10 PHA is capable of storing data for up to 16 samples.

The third subsystem shown in FIG. 5 is the computer 54 used for subsequent analysis of sample data. In one embodiment, only the sensor unit and PHA are carried into the field and the computer is left behind in a vehicle or at the central office. Sample data is collected in the field by the sensor unit and stored in the PHA. After the collection process is completed, the PHA is brought back and temporary connected to the computer to upload the stored spectrum data into the computer for further analysis.

In another embodiment, a portable computer, such as the Gridcase 2 computer, is used for analysis. Pulse height analyzers are available in the form of a printed circuit board that can be plugged directly into one of the expansion slots commonly found in most personal computers. In this configuration, the PHA card is housed within the case of the personal computer and is directly in communication with the computer bus. The PHA card is also connected by cable to the x-ray detector 15 in the sensor unit 10. All of these components can then be readily carried into the field. This arrangement allows complete analysis of sample on the site, without the need for subsequent analysis by a central computer.

The computer 54 performs a number of data processing functions. Spectrum data can be displayed in graphical form, as shown in FIG. 7. This allows the operator to view the spectrum data in a readily understandable form. The major peaks in the spectrum can be quickly identified and this information can be very helpful in a preliminary analysis to identify the major contaminants in the sample. The computer can also perform a qualitative analysis of the sample by matching the peaks in the spectrum data against previously stored data for a variety of elements. Finally, the computer provides a quantitative analysis of the relative concentrations of chemical elements present in a sample by comparing the relative heights of the peaks of the spectrum against the backscatter peaks of the x-ray tube and against a database of known peaks for a plurality of chemical elements.

Figure 6:
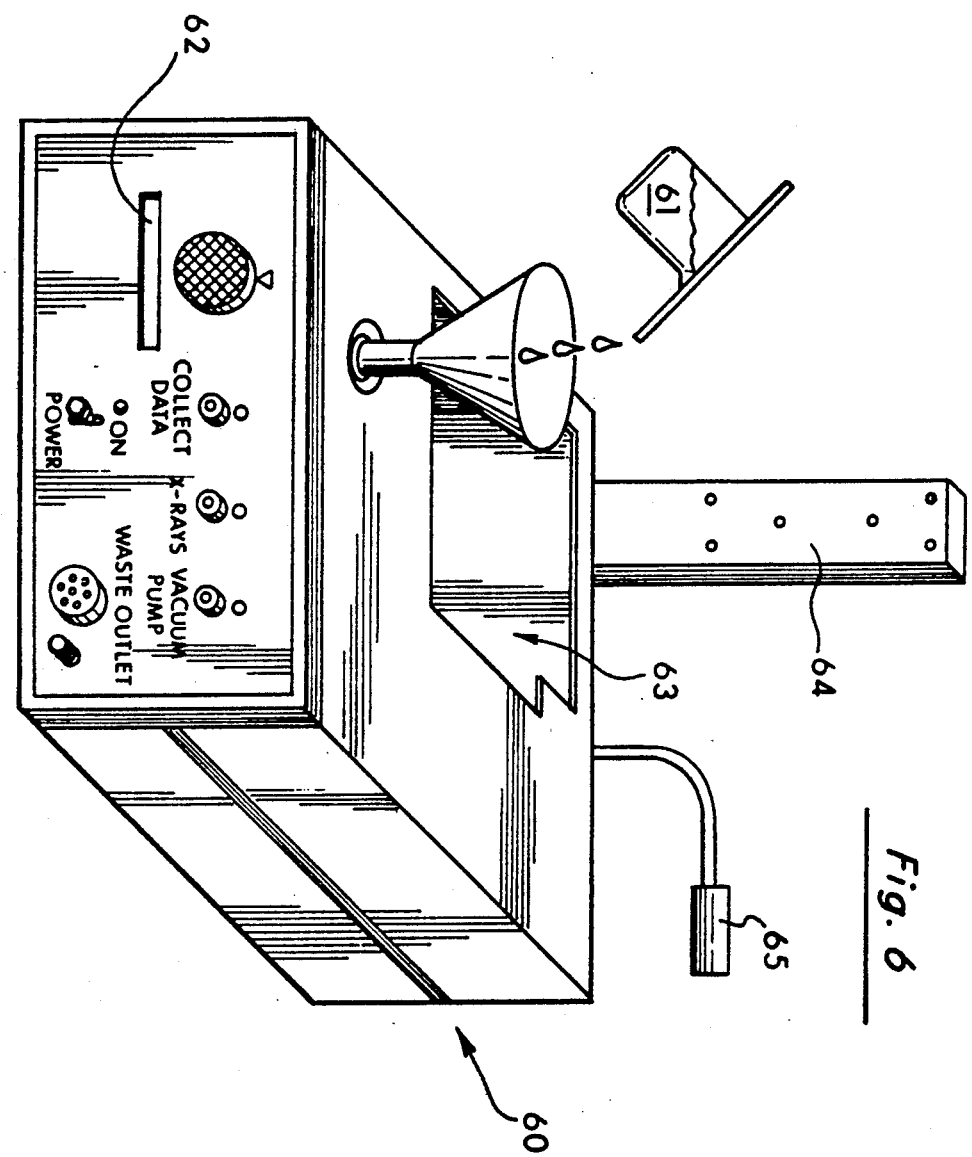
FIG. 6 is a perspective view of the filtration unit.

The last subsystem shown in FIG. 5 is the filtration enclosure 60. This subsystem is shown in greater detail in FIG. 6. First, a fresh filter in a suitable holder is placed into the filter carrier inlet 62 on the front of the filter enclosure 60. A liquid sample 61 containing suspended particles is then poured into the sample inlet funnel. The suspended particles are filtered out by the filter medium. The filtration enclosure can be used to filter particles not only from a naturally occurring suspension, but also to filter particles from a chemically created precipitate. This achieves much higher elemental sensitivities by extracting the metal ions in solution into a filterable solid phase collected on the filter medium. A vacuum pump is employed for the filtration process. The sensor unit 10 is placed in the opening 63 on the top of the filtration enclosure 60 so that sample particles trapped in the filter medium are positioned in the field of the x-ray beam produced by the x-ray tube 11 and are within the field of view of the x-ray detector 15. In this mode of operation, the battery connector 25 is disconnected and power input connector 65 from the filtration enclosure 60 is attached to the connector 27 on the side of the sensor unit 10 to power the high voltage power supply for the x-ray tube. This preserves the battery charge and allows for continuous operation of the x-ray tube. The size and shape of the opening 63 are determined to provide a clearance fit between the end of the sensor unit and the top of the filtration enclosure. This ensures accurate analysis by maintaining a proper spatial relationship between the sample particles on the filter medium in the filter enclosure 60 and the x-ray tube 11 and the detector 15 in the sensor unit 10. A support arm 64 is used to provide support and to maintain alignment of the sensor unit 10 with respect to the filtration enclosure 60.

The above disclosure sets forth a number of embodiments of the present invention. Other arrangements or embodiments, not precisely set forth, could be practiced under the teachings of the present invention and as set forth in the following claims.

We claim:

1. A portable x-ray fluorescence spectrometer comprising:
   a portable sensor unit having:
   (a) a battery;
   (b) a high voltage power supply powered by said battery;
   (c) an x-ray tube powered by said high voltage power supply and producing a beam of x-ray radiation direction toward an external sample located in a predetermined spatial relationship with respect to said sensor unit;
   (d) detector means adapted to detect the energy level of fluorescent x-rays produced by said sample;
   a pulse height analyzer in electrical connection with said detector means, adapted to generate a spectrum of data for each sample consisting of the number of fluorescent x-rays detected by said detector means as a function of the energy level of said fluorescent x-rays, and further adapted to store such data for a number of samples;
   a processing unit that can be removably attached to said pulse height analyzer, adapted to provide an analysis of the elemental composition of the sample by comparing the peaks in said spectrum against previously stored patterns of peaks for each of a plurality of chemical elements; and
   a filtration unit having:
   filtration means adapted to filter particles suspended in a fluid sample and collect said particles in a filtration medium; and
   positioning means adapted to removably secure said sensor unit to said filtration unit and position said sensor unit with respect to said filtration medium to permit analysis of said particles.

2. The portable x-ray fluorescence spectrometer of claim 1, wherein said detector means comprises a silicon-lithium semiconductor x-ray detector.

3. The portable x-ray fluorescence spectrometer of claim 2, further comprising cooling means adapted to cool said detector means.

4. The portable x-ray fluorescence spectrometer of claim 3, wherein said cooling means comprises a cryogenic storage tank containing liquid nitrogen to cool said detector.

5. The portable x-ray fluorescence spectrometer of claim 2, further comprising a sensor unit housing forming a metallic enclosure having an internal cavity, and further comprising a metallic divider within said cavity separating said high voltage power supply and said detector means.

6. The portable x-ray fluorescence spectrometer of claim 2, wherein said processing unit comprises a portable computer having a housing and number of internal expansion slots within said housing in electrical communication with said computer, and said pulse height analyzer comprises a printed circuit board within said computer housing inserted in one of said expansion slots and in electrical connection with the detector means of said sensor unit.

7. The portable x-ray fluorescence spectrometer of claim 2, wherein said processing unit further comprises means for generating a quantitive analysis of the relative concentrations of chemical elements present in a sample by comparing the relative heights of the peaks of said spectrum against the backscatter peaks of said x-ray tube and a data base for a plurality of chemical elements.

8. A portable x-ray fluorescence spectrometer comprising:
   a portable sensor unit containing within a housing:
   (a) a battery;
   (b) a high voltage power supply powered by said battery;
   (c) an x-ray tube powered by said high voltage power supply and producing a beam of x-ray radiation directed through an aperture in said housing toward an external sample located in a predetermined spatial relationship with respect to said sensor unit;
   (d) detector means adapted to detect the energy level of fluorescent x-rays produced by said sample;
   (e) electrical shielding separating said detector means and said high voltage power supply within said housing; and
   (f) a dewar flask adapted to contain liquid nitrogen to cool said detector means;
   a pulse height analyzer in electrical connection with said detector means, adapted to store fluorescent x-ray data generated by said detector means for a number of samples; and
   a processing unit that can be attached to said pulse height analyzer, adapted to provide elemental analysis of said data stored by said pulse height analyzer.

9. The portable x-ray fluorescence spectrometer of claim 8, further comprising a filtration unit having:
   filtration means adapted to filter particles suspended in a fluid sample and collect said particles in a filtration medium; and
   positioning means adapted to removably secure said sensor unit to said filtration unit and position said sensor unit with respect to said filtration medium to permit analysis of said sample particles.

10. The portable x-ray fluorescence spectrometer of claim 8, wherein said detector means comprises a silicon-lithium semiconductor x-ray detector.

11. The portable x-ray fluorescence spectrometer of claim 8, wherein said sensor unit housing comprises a metallic enclosure having an internal cavity, and said electrical shielding comprises a metallic divider within said cavity separating said high voltage power supply and said detector means.

12. The portable x-ray fluorescence spectrometer of claim 8, wherein said processing unit comprises a portable computer having a housing and number of internal expansion slots within said housing in electrical communication with said computer, and said pulse height analyzer comprises a printed circuit board within said computer housing inserted in one of said expansion slots and in electrical connection with the detector means of said sensor unit.

13. The portable x-ray fluorescence spectrometer of claim 8, wherein said processing unit further comprises means to graphically display a spectrum of the number of fluorescent x-rays detected for a sample as a function of the energy level of said fluorescent x-rays.

14. The portable x-ray fluorescence spectrometer of claim 8, wherein said processing unit further comprises means for generating a quantitative analysis of the relative concentrations of chemical elements present in a sample.

15. A portable x-ray fluorescence spectrometer comprising:
a portable sensor unit having:
  (a) a metallic housing having an interior cavity and an aperture extending from the interior cavity to the exterior of said housing;
  (b) a battery;
  (c) a metallic panel dividing the internal cavity of said housing into at least two separate chambers
  (d) a high voltage power supply powered by said battery, and located within the first of said chambers;
  (e) an x-ray tube within said housing powered by said high voltage power supply and producing a beam of x-ray radiation directed through said aperture to irradiate an external sample;
  (f) a silicon-lithium semiconductor x-ray detector located within the second of said chambers adapted to detect the energy level of fluorescent x-rays produced by said sample passing through said aperture; and
  (g) cooling means adapted to cool said x-ray detector;
a pulse height analyzer in electrical connection with said detector, adapted to store fluorescent x-ray data generated by said detector for a number of samples;
a processing unit that can be attached to said pulse height analyzer, adapted to provide elemental analysis of said data stored by said pulse height analyzer; and
a filtration unit having:
  (a) filtration means adapted to filter particles suspended in a fluid sample and collect said particles in a filtration medium; and
  (b) positioning means adapted to removably secure said sensor unit to said filtration unit and position said sensor unit with respect to said filtration medium to permit analysis of said sample particles.

16. The portable x-ray fluorescence spectrometer of claim 15, wherein said processing unit comprises a portable computer having a housing and number of internal expansion slots within said housing in electrical communication with said computer, and said pulse height analyzer comprises a printed circuit board within said computer housing inserted in one of said expansion slots and in electrical connection with the detector means of said sensor unit 17. The portable x-ray fluorescence spectrometer of claim 15, wherein said processing unit further comprises means to graphically display a spectrum of the number of fluorescent x-rays detected for a sample as a function of the energy level of said fluorescent x-rays.

18. The portable x-ray fluorescence spectrometer of claim 15, wherein said processing unit further comprises means for generating a quantitative analysis of the relative concentrations of chemical elements present in a sample.

19. A portable x-ray fluorescence spectrometer comprising:
a portable sensor unit having:
  (a) a metallic housing having an interior cavity and an aperture extending from the interior cavity to the exterior of said housing;
  (b) a battery;
  (c) a metallic panel dividing the internal cavity of said housing into at least two separate chambers
  (d) a high voltage power supply powered by said battery, and located within the first of said chambers;
  (e) an x-ray tube within said housing powered by said high voltage power supply and producing a beam of x-ray radiation directed through said aperture to irradiate an external sample;
  (f) a silicon-lithium semiconductor x-ray detector located within the second of said chambers adapted to detect the energy level of fluorescent x-rays produced by said sample passing through said aperture; and
  (g) a dewar flask adapted to contain liquid nitrogen to cool said x-ray detector; and
a portable computer having:
  (a) a housing and number of internal expansion slots within said housing in electrical communication with said computer; and
  (b) a pulse height analyzer within said computer housing inserted in one of said expansion slots and in electrical connection with the detector of said sensor unit, adapted to generate a spectrum of data for each sample consisting of the number of fluorescent x-rays detected by said detector means as a function of the energy level of said fluorescent x-rays; and
  (c) data processing means connected to said expansion slots, adapted to provide an analysis of the elemental composition of the sample by comparing the peaks in said spectrum against the backscatter peaks of said x-ray tube and a data base for a plurality of chemical elements.

20. The portable x-ray fluorescence spectrometer of claim 19, further comprising a filtration unit having:
filtration means adapted to filter particles suspended in a fluid sample and collect said particles in a filtration medium; and
positioning means adapted to removably secure said sensor unit to said filtration unit and position said sensor unit with respect to said filtration medium to permit analysis of said sample particles.

21. The portable x-ray fluorescence spectrometer of claim 19, wherein said data processing means further comprises means to graphically display a spectrum of the number of fluorescent x-rays detected for a sample as a function of the energy level of said fluorescent x-rays.

22. The portable x-ray fluorescence spectrometer of claim 19, wherein said data processing means further comprises means for generating a quantitative analysis of the relative concentrations of chemical elements present in a sample by comparing the relative heights of the peaks of said spectrum against the backscatter peaks of said x-ray tube and a data base for a plurality of chemical elements.

* * * * *

UNITED STATES PATENT AND TRADEMARK OFFICE
CERTIFICATE OF CORRECTION

PATENT NO. : 5,014,287
DATED : May 7, 1991
INVENTOR(S) : Michael G. Thornton, et al.

It is certified that error appears in the above-indentified patent and that said Letters Patent is hereby corrected as shown below:

On the title page, item [76]   add the following as a third co-inventor:
        Warren C. Kelliher, 4406 Victoria Blvd., Hampton, Virginia   23669

Signed and Sealed this

Tenth Day of February, 1998

*Attest:*

BRUCE LEHMAN

*Attesting Officer*      Commissioner of Patents and Trademarks